US005652133A

United States Patent [19]

Murphy

[11] Patent Number: 5,652,133

[45] Date of Patent: Jul. 29, 1997

[54] CLONING AND EXPRESSION OF THE HUMAN MACROPHAGE INFLAMMATORY PROTEIN-1α(MIP-1 α) /RANTES RECEPTOR

[75] Inventor: Philip M. Murphy, Rockville, Md.

[73] Assignee: The United States of America as represented by the Secretary of the Department of Health and Human Services, Washington, D.C.

[21] Appl. No.: 12,988

[22] Filed: Jan. 28, 1993

[51] Int. Cl.[6] .......................... C12N 15/12; C07K 14/705

[52] U.S. Cl. ........................ 435/325; 536/23.1; 536/23.5; 536/24.31; 435/6; 435/320.1; 435/357; 435/365; 530/350; 530/351

[58] Field of Search ................................ 536/23.1, 23.5, 536/24.3, 24.31, 24.33; 435/6, 240.2, 252.3, 320.1; 530/351, 350

[56] References Cited

U.S. PATENT DOCUMENTS 4,985,352 1/1991 Julius et al. ................................ 435/6

OTHER PUBLICATIONS

Sambrook, J. et al., *Molecular Cloning : A Laboratory Manual*, Cold Spring Harbor Laboratory Press, 1989, p. 1415.

Gao et al., *J. Exp. Med.*, 177(5): 1421–1427, 1993.

Holmes, W.E. et al., *Science*, 253: 1278–80, 1991.

Murphy, P.M. et al., *Science*, 253:1280–1283, 1991.

Rot A. et al., *J. Exp. Med.*, 176:1489–95, Dec. 1992.

Neote, K. et al., *FASEB J.*, 6(5):A2054, abstract 6475, Apr. 1992.

*Primary Examiner*—Marianne P. Allen

*Attorney, Agent, or Firm*—Townsend and Townsend and Crew LLP

[57] ABSTRACT

This invention provides for the cloning and expression of the human Macrophage Inflammatory Protein-1α (MIP-1α)/ RANTES Receptor. This receptor binds two cytokines MIP-1α and RANTES which are pro-inflammatory cytokines. The receptor is useful for assaying the levels of these cytokines in biological specimens. These cytokines play key roles in the inflammatory processes afflicting man.

12 Claims, 2 Drawing Sheets

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 2156 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: primer_bind
( B ) LOCATION: 259..275

( i x ) FEATURE:
( A ) NAME/KEY: primer_bind
( B ) LOCATION: complement (868..884)

( i x ) FEATURE:
( A ) NAME/KEY: CDS
( B ) LOCATION: 63..1128

( x i ) SEQUENCE DESCRIPTION: SEQ ID NO:1:

GGCACGAGCC CAGAAACAAA GACTTCACGG ACAAAGTCCC TTGGAACCAG AGAGAAGCCG 60

GG ATG GAA ACT CCA AAC ACC ACA GAG GAC TAT GAC ACG ACC ACA GAG 107

-continued

```
    Met Glu Thr Pro Asn Thr Thr Glu Asp Tyr Asp Thr Thr Thr Glu
     1               5                  10                  15

TTT GAC TAT GGG GAT GCA ACT CCG TGC CAG AAG GTG AAC GAG AGG GCC    155
Phe Asp Tyr Gly Asp Ala Thr Pro Cys Gln Lys Val Asn Glu Arg Ala
                 20                  25                  30

TTT GGG GCC CAA CTG CTG CCC CCT CTG TAC TCC TTG GTA TTT GTC ATT    203
Phe Gly Ala Gln Leu Leu Pro Pro Leu Tyr Ser Leu Val Phe Val Ile
             35                  40                  45

GGC CTG GTT GGA AAC ATC CTG GTG GTC CTG GTC CTT GTG CAA TAC AAG    251
Gly Leu Val Gly Asn Ile Leu Val Val Leu Val Leu Val Gln Tyr Lys
         50                  55                  60

AGG CTA AAA AAC ATG ACC AGC ATC TAC CTC CTG AAC CTG GCC ATT TCT    299
Arg Leu Lys Asn Met Thr Ser Ile Tyr Leu Leu Asn Leu Ala Ile Ser
     65                  70                  75

GAC CTG CTC TTC CTG TTC ACG CTT CCC TTC TGG ATC GAC TAC AAG TTG    347
Asp Leu Leu Phe Leu Phe Thr Leu Pro Phe Trp Ile Asp Tyr Lys Leu
 80                  85                  90                  95

AAG GAT GAC TGG GTT TTT GGT GAT GCC ATG TGT AAG ATC CTC TCT GGG    395
Lys Asp Asp Trp Val Phe Gly Asp Ala Met Cys Lys Ile Leu Ser Gly
                100                 105                 110

TTT TAT TAC ACA GGC TTG TAC AGC GAG ATC TTT TTC ATC ATC CTG CTG    443
Phe Tyr Tyr Thr Gly Leu Tyr Ser Glu Ile Phe Phe Ile Ile Leu Leu
            115                 120                 125

ACG ATT GAC AGG TAC CTG GCC ATC GTC CAC GCC GTG TTT GCC TTG CGG    491
Thr Ile Asp Arg Tyr Leu Ala Ile Val His Ala Val Phe Ala Leu Arg
        130                 135                 140

GCA CGG ACC GTC ACT TTT GGT GTC ATC ACC AGC ATC ATC ATT TGG GCC    539
Ala Arg Thr Val Thr Phe Gly Val Ile Thr Ser Ile Ile Ile Trp Ala
    145                 150                 155

CTG GCC ATC TTG GCT TCC ATG CCA GGC TTA TAC TTT TCC AAG ACC CAA    587
Leu Ala Ile Leu Ala Ser Met Pro Gly Leu Tyr Phe Ser Lys Thr Gln
160                 165                 170                 175

TGG GAA TTC ACT CAC CAC ACC TGC AGC CTT CAC TTT CCT CAC GAA AGC    635
Trp Glu Phe Thr His His Thr Cys Ser Leu His Phe Pro His Glu Ser
                180                 185                 190

CTA CGA GAG TGG AAG CTG TTT CAG GCT CTG AAA CTG AAC CTC TTT GGG    683
Leu Arg Glu Trp Lys Leu Phe Gln Ala Leu Lys Leu Asn Leu Phe Gly
            195                 200                 205

CTG GTA TTG CCT TTG TTG GTC ATG ATC ATC TGC TAC ACA GGG ATT ATA    731
Leu Val Leu Pro Leu Leu Val Met Ile Ile Cys Tyr Thr Gly Ile Ile
        210                 215                 220

AAG ATT CTG CTA AGA CGA CCA AAT GAG AAG AAA TCC AAA GCT GTC CGT    779
Lys Ile Leu Leu Arg Arg Pro Asn Glu Lys Lys Ser Lys Ala Val Arg
    225                 230                 235

TTG ATT TTT GTC ATC ATG ATC ATC TTT TTT CTC TTT TGG ACC CCC TAC    827
Leu Ile Phe Val Ile Met Ile Ile Phe Phe Leu Phe Trp Thr Pro Tyr
240                 245                 250                 255

AAT TTG ACT ATA CTT ATT TCT GTT TTC CAA GAC TTC CTG TTC ACC CAT    875
Asn Leu Thr Ile Leu Ile Ser Val Phe Gln Asp Phe Leu Phe Thr His
                260                 265                 270

GAG TGT GAG CAG AGC AGA CAT TTG GAC CTG GCT GTG CAA GTG ACG GAG    923
Glu Cys Glu Gln Ser Arg His Leu Asp Leu Ala Val Gln Val Thr Glu
            275                 280                 285

GTG ATC GCC TAC ACG CAC TGC TGT GTC AAC CCA GTG ATC TAC GCC TTC    971
Val Ile Ala Tyr Thr His Cys Cys Val Asn Pro Val Ile Tyr Ala Phe
        290                 295                 300

GTT GGT GAG AGG TTC CGG AAG TAC CTG CGG CAG TTG TTC CAC AGG CGT   1019
Val Gly Glu Arg Phe Arg Lys Tyr Leu Arg Gln Leu Phe His Arg Arg
    305                 310                 315
```

-continued

```
GTG GCT GTG CAC CTG GTT AAA TGG CTC CCC TTC CTC TCC GTG GAC AGG      1067
Val Ala Val His Leu Val Lys Trp Leu Pro Phe Leu Ser Val Asp Arg
320                 325                 330                 335

CTG GAG AGG GTC AGC TCC ACA TCT CCC TCC ACA GGG GAG CAT GAA CTC      1115
Leu Glu Arg Val Ser Ser Thr Ser Pro Ser Thr Gly Glu His Glu Leu
                340                 345                 350

TCT GCT GGG TTC T GACTCAGACC ATAGGAGGCC AACCCAAAAT AAGCAGGCGT        1168
Ser Ala Gly Phe
            355

GACCTGCCAG GCACACTGAG CCAGCAGCCT GGCTCTCCCA GCCAGGTTCT GACTCTTGGC    1228

ACAGCATGGA GTCACAGCCA CTTGGGATAG AGAGGGAATG TAATGGTGGC CTGGGGCTTC    1288

TGAGGCTTCT GGGGCTTCAG TCTTTTCCAT GAACTTCTCC CCTGGTAGAA AGAAGATGAA    1348

TGAGCAAAAC CAAATATTCC AGAGACTGGG ACTAAGTGTA CCAGAGAAGG GCTTGGACTC    1408

AAGCAAGATT TCAGATTTGT GACCATTAGC ATTTGTCAAC AAAGTCACCC ACTTCCCACT    1468

ATTGCTTGCA CAAACCAATT AAACCCAGTA GTGGTGACTG TGGGCTCCAT TCAAAGTGAG    1528

CTCCTAAGCC ATGGGAGACA CTGATGTATG AGGAATTTCT GTTCTTCCAT CACCTCCCCC    1588

CCCCCGCCAC CCTCCCACTG CCAAGAACTT GGAAATAGTG ATTTCCACAG TGACTCCACT    1648

CTGAGTCCCA GAGCCAATCA GTAGCCAGCA TCTGCCTCCC CTTCACTCCC ACCGCAGGAT    1708

TTGGGCTCTT GGAATCCTGG GGAACATAGA ACTCATGACG GAAGAGTTGA GACCTAACGA    1768

GAAATAGAAA TGGGGGAACT ACTGCTGGCA GTGGAACTAA GAAAGCCCTT AGGAAGAATT    1828

TTTATATCCA CTAAAATCAA ACAATTCAGG GAGTGGGCTA AGCACGGGCC ATATGAATAA    1888

CATGGTGTGC TTCTTAAAAT AGCCATAAAG GGGAGGGACT CATCATTTCC ATTTACCCTT    1948

CTTTTCTGAC TATTTTTCAG AATCTCTCTT CTTTTCAAGT TGGGTGATAT GTTGGTAGAT    2008

TCTAATGGCT TTATTGCAGC GATTAATAAC AGGCAAAAGG AAGCAGGGTT GGTTTCCCTT    2068

CTTTTTGTTC TTCATCTAAG CCTTCTGGTT TTATGGGTCA GAGTTCCGAC TGCCATCTTG    2128

GACTTGTCAG CAAAAAAAAA AAAAAAAA                                       2156
```

( 2 ) INFORMATION FOR SEQ ID NO:2:

( i ) SEQUENCE CHARACTERISTICS:
( A ) LENGTH: 355 amino acids
( B ) TYPE: amino acid
( D ) TOPOLOGY: linear ( i i ) MOLECULE TYPE: protein ( x i ) SEQUENCE DESCRIPTION: SEQ ID NO:2:

```
Met Glu Thr Pro Asn Thr Thr Glu Asp Tyr Asp Thr Thr Thr Glu Phe
  1               5                  10                  15

Asp Tyr Gly Asp Ala Thr Pro Cys Gln Lys Val Asn Glu Arg Ala Phe
             20                  25                  30

Gly Ala Gln Leu Leu Pro Pro Leu Tyr Ser Leu Val Phe Val Ile Gly
         35                  40                  45

Leu Val Gly Asn Ile Leu Val Val Leu Val Leu Val Gln Tyr Lys Arg
     50                  55                  60

Leu Lys Asn Met Thr Ser Ile Tyr Leu Leu Asn Leu Ala Ile Ser Asp
 65                  70                  75                  80

Leu Leu Phe Leu Phe Thr Leu Pro Phe Trp Ile Asp Tyr Lys Leu Lys
                 85                  90                  95

Asp Asp Trp Val Phe Gly Asp Ala Met Cys Lys Ile Leu Ser Gly Phe
            100                 105                 110
```

-continued

| | | | | | | | | | | | | | | | |
|---|---|---|---|---|---|---|---|---|---|---|---|---|---|---|---|
| Tyr | Tyr | Thr | Gly | Leu | Tyr | Ser | Glu | Ile | Phe | Phe | Ile | Ile | Leu | Leu | Thr |
| | | 115 | | | | | 120 | | | | | 125 | | | |
| Ile | Asp | Arg | Tyr | Leu | Ala | Ile | Val | His | Ala | Val | Phe | Ala | Leu | Arg | Ala |
| | 130 | | | | | 135 | | | | | 140 | | | | |
| Arg | Thr | Val | Thr | Phe | Gly | Val | Ile | Thr | Ser | Ile | Ile | Ile | Trp | Ala | Leu |
| 145 | | | | | 150 | | | | | 155 | | | | | 160 |
| Ala | Ile | Leu | Ala | Ser | Met | Pro | Gly | Leu | Tyr | Phe | Ser | Lys | Thr | Gln | Trp |
| | | | | 165 | | | | | 170 | | | | | 175 | |
| Glu | Phe | Thr | His | His | Thr | Cys | Ser | Leu | His | Phe | Pro | His | Glu | Ser | Leu |
| | | | 180 | | | | | 185 | | | | | 190 | | |
| Arg | Glu | Trp | Lys | Leu | Phe | Gln | Ala | Leu | Lys | Leu | Asn | Leu | Phe | Gly | Leu |
| | | 195 | | | | | 200 | | | | | 205 | | | |
| Val | Leu | Pro | Leu | Leu | Val | Met | Ile | Ile | Cys | Tyr | Thr | Gly | Ile | Ile | Lys |
| | 210 | | | | | 215 | | | | | 220 | | | | |
| Ile | Leu | Leu | Arg | Arg | Pro | Asn | Glu | Lys | Lys | Ser | Lys | Ala | Val | Arg | Leu |
| 225 | | | | | 230 | | | | | 235 | | | | | 240 |
| Ile | Phe | Val | Ile | Met | Ile | Ile | Phe | Phe | Leu | Phe | Trp | Thr | Pro | Tyr | Asn |
| | | | | 245 | | | | | 250 | | | | | 255 | |
| Leu | Thr | Ile | Leu | Ile | Ser | Val | Phe | Gln | Asp | Phe | Leu | Phe | Thr | His | Glu |
| | | | 260 | | | | | 265 | | | | | 270 | | |
| Cys | Glu | Gln | Ser | Arg | His | Leu | Asp | Leu | Ala | Val | Gln | Val | Thr | Glu | Val |
| | | 275 | | | | | 280 | | | | | 285 | | | |
| Ile | Ala | Tyr | Thr | His | Cys | Cys | Val | Asn | Pro | Val | Ile | Tyr | Ala | Phe | Val |
| | 290 | | | | | 295 | | | | | 300 | | | | |
| Gly | Glu | Arg | Phe | Arg | Lys | Tyr | Leu | Arg | Gln | Leu | Phe | His | Arg | Arg | Val |
| 305 | | | | | 310 | | | | | 315 | | | | | 320 |
| Ala | Val | His | Leu | Val | Lys | Trp | Leu | Pro | Phe | Leu | Ser | Val | Asp | Arg | Leu |
| | | | | 325 | | | | | 330 | | | | | 335 | |
| Glu | Arg | Val | Ser | Ser | Thr | Ser | Pro | Ser | Thr | Gly | Glu | His | Glu | Leu | Ser |
| | | | 340 | | | | | 345 | | | | | 350 | | |
| Ala | Gly | Phe | | | | | | | | | | | | | |
| | | 355 | | | | | | | | | | | | | |

CLONING AND EXPRESSION OF THE HUMAN MACROPHAGE INFLAMMATORY PROTEIN-1α(MIP-1 α) /RANTES RECEPTOR

BACKGROUND OF THE INVENTION

This invention provides for the cloning and expression of the human Macrophage Inflammatory Protein-1α (MIP-1α) /RANTES Receptor. This receptor binds two cytokines MIP-1α and RANTES which are pro-inflammatory cytokines. The receptor is useful for assaying the levels of these cytokines in biological specimens. These cytokines play key roles in the inflammatory processes afflicting man.

The chemokine β division of the platelet factor 4 superfamily is comprised of at least six distinct cytokines that regulate trafficking of phagocytes and lymphocytes in mammalian species; at least one of these, MIP-1α also possesses anti-proliferative activity for hematopoietic stem cells. MIP-1α and the related β chemokine, RANTES, induce transient alterations in intracellular $Ca^{2+}$ concentration in neutrophils that can be reciprocally and specifically desensitized, suggesting a common receptor. This invention provides both the cDNA and the gene for this receptor. The receptor is a member of the G protein-coupled receptor superfamily. It has ~33% amino acid identity with receptors for the α chemokine, interleukin-8, and may be the human homologue of the product of US28, an open reading frame of human cytomegalovirus.

The platelet factor 4 cytokine superfamily is comprised of structurally and functionally related 8–10 kilodalton peptides that are the products of distinct genes clustered on human chromosomes 4 and 17. The superfamily was named after the first member to be characterized. These peptides have been collectively designated as "chemokines" because of their hybrid activities: they regulate the trafficking and activation of lymphocytes and phagocytes of the mammalian immune system, but in addition, some are able to regulate the proliferative potential of hematopoietic progenitor cells, endothelial cells, and certain types of transformed cells (for reviews see Wolpe and Cerami, *FASEB J.* 3, 2565–2573 (1989); Oppenheim et al., *Immunol.* 9, 617–648 (1991); Schall, *Cytokine* 3, 165–183 (1991)). Thus, the chemokines are thought to play an important role in host defense against infection, in the pathogenesis of chronic inflammatory disorders, and in wound healing.

A structural signature common to all chemokines is the presence of four conserved cysteine residues. The chemokines can be divided into two groups, α and β, by the arrangement of the first two of these cysteines. Members of the chemokine α group all possess a single amino acid of variable identity interposed between the first two cysteines, the so-called "C—X—C" motif. The human chemokine α family includes platelet factor 4, interleukin-8/neutrophil activating peptide-1 (IL-8), GROα/melanoma growth stimulatory activity (GROα/MGSA), neutrophil activating peptide-2 (NAP-2), and other less well-characterized molecules. In general, members of this group are potent chemoattractants for neutrophils in vivo and in vitro; IL-8 and platelet factor 4 also regulate angiogenesis. (Koch et al., *Science* 258, 1798–1801 (1992); Maione et al., *Science* 247, 77–79 (1990)). Two human chemokine α receptors, designated IL-8 receptors A and B, have been identified; their structures are 77% identical at the amino acid level. IL-8 receptor B is a receptor for IL-8, NAP-2 and GROα/MGSA (Murphy and Tiffany, *Science* 253, 1280–1283 (1991); Lee et al., *J. Biol. Chem.* 267, 16283–16287 (1992)) whereas IL-8 receptor A is more selective for IL-8 (Holmes et al., *Science* 253, 1278–1280 (1991); Lee et al., *J. Biol. Chem.* 267, 16283–16287 (1992)). Signal transduction by both receptor subtypes leads to a rapid rise in the intracellular concentration of $Ca^{2+}$.

In contrast, the first two conserved cysteines of all members of the chemokine β group are adjacent, the "C—C" motif. Members of this group attract and activate neutrophils, eosinophils, monocytes, macrophages and lymphocytes with variable selectivity. The human chemokine β family includes MIP-1α (Macrophage Inflammatory Protein-1α), MIP-1β, RANTES (Regulated on Activation, Normal T Expressed and Secreted), MCP-1 (Monocyte Chemoattractant Protein-1), MCP-2, MCP-3 and I-309. Of these, the biological properties of MIP-1α, RANTES and MCP-1 have been the most characterized.

Murine MIP-1 was originally purified from supernatants of endotoxin-activated macrophages as a complex of MIP-1α and MIP-1β which are 67% identical in amino acid sequence (Wolpe et al., *J. Exp. Med.* 167, 570–581 (1988); Davatelis et al., *J. Exp. Med.* 167, 1939–1944 (1988); Sherry et al., *J. Exp. Med.* 168, 2251–2259 (1988)).

In addition to being a chemoattractant for neutrophils (Wolpe et al., *J. Exp. Med.* 167, 570–581 (1988); Saukkonen et al., *J. Exp. Med.* 171, 439–448 (1990)), murine MIP-1 is a prostaglandin-independent endogenous pyrogen, has autocrine effects on macrophages, and may be involved in wound healing (Davatelis et al., *Science* 243, 1066–1068 (1989); Fahey et al., *J. Immunol.* 148, 2764–2769 (1992); Fahey et al., *Cytokine* 2, 92–98 (1990)). Many if not all of these effects are due to MIP-1α. In addition, MIP-1α suppresses proliferation of hematopoietic stem cells (Graham et al., *Nature* 344, 442–444 (1990); Broxmeyer et al., *Blood* 76, 1110–1116 (1990); Broxmeyer et al., *J. Immunol.* 147, 2586–2594 (1991); Dunlop et al., *Blood* 79, 2221–2225 (1992)). For this reason it has been suggested that MIP-1α may be a useful cytoprotective agent for clinical radiotherapy and chemotherapy of neoplastic disease (Dunlop et al., *Blood* 79, 2221–2225 (1992)). Limited functional information for MIP-1α using the human ligand and human targets is available. High and low affinity binding sites have been reported for human MIP-1α on the human myeloid cell line U937 (Yamamura et ai., *Int. J. Hematol.* 55, 131–137 (1992)); in contrast, a single class of binding sites for murine MIP-1α was detected on murine T cell and macrophage cell lines (Oh et al., *J. Immunol.* 147, 2978–2983 (1991)).

RANTES attracts eosinophils, monocytes and "memory" T cells ($CD4^+$/$CD45RO^+$). It is a weak chemoattractant for neutrophils (Kameyoshi et ai., *J. Exp. Med.* 176, 587–592 (1992); Schall et al., *Nature* 347, 669–671 (1990); Schall, Cytokine 3, 165–183 (1991)). Characterization of binding sites for RANTES has not yet been reported. MCP-1 is a potent and specific chemoattractant and activating factor for monocytes (reviewed in Matsushima and Oppenheim, Cytokine 1, 2–13(1989)). Binding sites have been detected for MCP-1 on human monocytes (Yoshimura and Leonard, *J. Immunol.* 145, 292–297 (1990)).

SUMMARY OF THE INVENTION

This invention provides for a substantially purified nucleic acid encoding a receptor for macrophage inflammatory protein-1α (MIP-1α) and reduced upon activation normal T expressed and secreted (RANTES) protein said nucleic acid having a sequence substantially identical to a nucleic acid of Sequence I.D. No. 1 or the corresponding RNA. This invention further provides for primers and probes specific for this nucleic acid which comprise at least 12 contiguous nucleotides. Said sequences are then compared with known sequences by computer to determine their specificity in the human genome.

These nucleic acids are useful for expression in recombinant hosts operably linked to a promoter which is part of an expression cassette. The expression typically occurs as part of an expression vector or plasmid. The vector is then transformed into a host cell, preferably a mammalian cell. Functional expression whereby the receptor in an active form is expressed and transported to the plasma membrane of a cell is also described herein.

In addition this invention provides for purified recombinantly produced MIP-1α and RANTES protein from the nucleic acids described herein.

This invention further provides for a method of detecting the presence, absence or amount of cytokines RANTES and MIP-1α in a sample such as a physiological specimen, said method comprising:

(i) transforming a mammalian cell with a nucleic acid encoding a receptor for macrophage inflammatory protein-1α (MIP-1α) and reduced upon activation normal T expressed and secreted (RANTES) protein said nucleic acid having a sequence substantially identical to a nucleic acid of Sequence I.D. No. 1;

(ii) culturing the cell under conditions permitting the expression of the receptor and its transport to the plasma membrane of the cell;

(iii) contacting the cell with a cytokine selected from the group consisting of RANTES and MIP-1α; and, (iv) detecting the binding of the cytokines to the receptor. In preferred formats the cells are oocytes, the nucleic acid is either cDNA or cRNA and the detection step is by measuring calcium mobilization or direct assay of the cytokine on the plasma membrane.

In another embodiment, the invention provides for assays in which activated neutrophils or any other cell producing the MIP-1α/RANTES receptor are used. Said cells would rely upon endogenous genes for the production of the receptor. The methods for use of endogenous receptor containing cells are as described herein for the recombinantly transformed cells.

DEFINITIONS

Figure 1A:
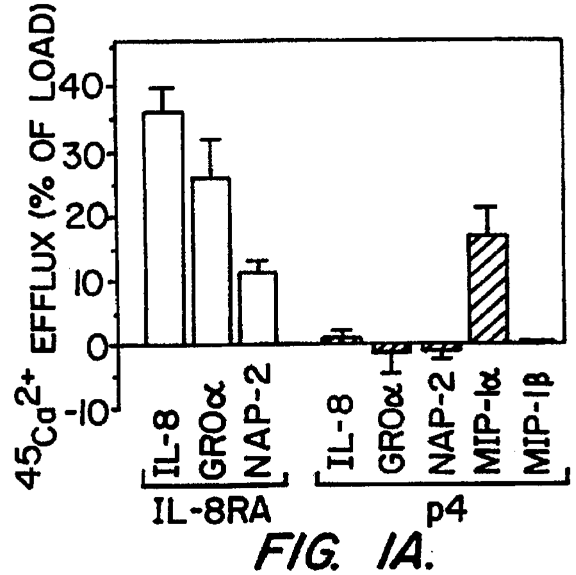
FIGS. 1A–C. Signal transduction by the receptor. (A) This chart presents evidence that the described cDNA encodes a receptor selective for an intercrine β ligand. (B) This chart provides concentration dependence for MIP-1α calcium mobilizing activity. (C) This chart presents data evidencing that the MIP-1α receptor is also a receptor for RANTES.

The phrase "nucleic acid sequence" refers to a single or double-stranded polymer of deoxyribonucleotide or ribonucleotide bases read from the 5' to the 3' end. It includes both self-replicating plasmids, infectious polymers of DNA or RNA and non-functional DNA or RNA.

Nucleic acids, as used herein, may be DNA or RNA. Additionally, substantial nucleic acid sequence identity exists when a nucleic acid segment will hybridize under selective hybridization conditions, to a complement of another nucleic acid strand under stringent hybridization conditions. Thus a given sequence can be varied to a minor degree and without effecting its ability to bind to a predetermined target. Typically a nucleic acid will hybridize to other sequences that are almost identical if the stringency conditions are reduced. The sequences of this invention are considered substantially identical if the sequences are able to bind under the following highly stringent conditions: 68° C. and 0.1× SSC or SSPE. Typically this means that the sequences are at least 75% homologous. However, when the signals are at optimum levels, one is assured that the sequences are essentially identical having about 90% homology. Thus, the invention provides for orthologous non-human MIP-1α/RANTES receptors.

The phrase "calcium mobilization" refers to the release of calcium ions from intracellular stores into the cytoplasm. This is often accompanied by an influx of calcium ions from the extracellular fluid (environment) into the cytoplasm. The final event is the pumping of cytoplasmic calcium into the extracellular fluid which is known as efflux and measured by release of radioactive calcium or by fluorescent means.

The term "complementary" means that one nucleic acid is identical to, or hybridizes selectively to, another nucleic acid. Typically, selective hybridization will occur when there is at least about 55% identity over a stretch of at least 14–25 nucleotides, preferably at least about 65%, more preferably at least about 75%, and most preferably at least about 90%. See, M. Kanehisa *Nucleic Acids Res.* 12:203 (1984), incorporated herein by reference.

"Isolated" or "substantially pure", when referring to nucleic acids, refer to those that have been purified away from other cellular components or other contaminants, e.g., other cellular nucleic acids or proteins, by standard techniques, including alkaline/SDS treatment, CsCl banding, column chromatography, and others well known in the art. See, F. Ausubel, et al., ed. *Current Protocols in Molecular Biology*, Greene Publishing and Wiley-Interscience, New York (1987), incorporated herein by reference.

"Nucleic acid probes" may be DNA fragments prepared, for example, by PCR as discussed above, or synthesized by either the phosphoramidite method described by Beaucage and Carruthers, *Tetrahedron Lett.* 22:1859–1862 (1981), or by the triester method according to Matteucci, et al., *J. Am. Chem. Soc.,* 103:3185 (1981), both incorporated herein by reference. A double stranded fragment may then be obtained, if desired, by annealing the chemically synthesized single strands together under appropriate conditions or by synthesizing the complementary strand using DNA polymerase with an appropriate primer sequence. Where a specific nucleic acid sequence is given, it is understood that the complementary strand is also identified and included. The complementary strand will work equally well in situations where the target is a double stranded nucleic acid.

A nucleic acid probe is complementary to a target nucleic acid when it will anneal only to a single desired position on that target nucleic acid under conditions described herein. Proper annealing conditions depend, for example, upon a probe's length, base composition, and the number of mismatches and their position on the probe, and must often be determined empirically. For discussions of nucleic acid probe design and annealing conditions, see, for example, Sambrook et al., *Molecular Cloning: A Laboratory Manual* (2nd ed.), Vols. 1–3, Cold Spring Harbor Laboratory, (1989)

or *Current Protocols in Molecular Biology*, F. Ausubel et al., ed. Greene Publishing and Wiley-Interscience, New York (1987), both of which are incorporated herein by reference.

The term "promoter" refers to a region of DNA upstream from the structural gene and involved in recognition and binding RNA polymerase and other proteins to initiate transcription.

The term "operably linked" refers to functional linkage between a promoter and a second sequence, wherein the promoter sequence initiates transcription of RNA corresponding to the second sequence. Generally, operably linked means that the nucleic acid sequences being linked are contiguous and, where necessary to join two protein coding regions, contiguous and in reading frame.

Techniques for nucleic acid manipulation, such as subcloning nucleic acid sequences encoding polypeptides into expression vectors, labelling probes, DNA hybridization, and so on are described generally, for example in Sambrook et al. (1989) op. cit., or Ausubel et al., ed. (1987) op. cit., both of which are incorporated herein by reference.

"Expression vectors", "cloning vectors", or "vectors" are often plasmids or other nucleic acid molecules that are able to replicate in a chosen host cell. Expression vectors may replicate autonomously, or they may replicate by being inserted into the genome of the host cell, by methods well known in the art. Vectors that replicate autonomously will have an origin of replication or autonomous replicating sequence (ARS) that is functional in the chosen host cell(s). Often, it is desirable for a vector to be usable in more than one host cell, e.g., in *E. coli* for cloning and construction, and in a mammalian cell for expression.

The phrase, "MIP-1α/RANTES receptor" refers to the gene product encoded by Seq. I.D. No. 1 and includes naturally occurring polymorphic variants in human and non-human populations which would be detectable using the given sequence as hybridization probe. In addition the term includes minor or conservative substitutions, deletions and additions to the primary amino acid sequence which do not significantly alter the biological properties of the native protein. Such changes would include substitutions of amino acids having similar chemical properties such as aspartic acid for glutamic acid or lysine for arginine and the like.

The terms "peptide", "polypeptide" or "protein" are used interchangeably herein. The term "substantial identity", when referring to polypeptides, indicates that the polypeptide or protein in question is at least about 70% identical to an entire naturally occurring protein (native) or a portion thereof, and preferably at least about 95% identical. Thus, the invention embraces orthologous non-human MIP-1α/RANTES receptors.

As used herein, the terms "isolated" and "substantially pure" are used interchangeably and describe a protein that has been separated from components which naturally accompany it. Typically, a monomeric protein is substantially pure when at least about 60 to 75% of a sample exhibits a single polypeptide backbone. Minor variants or chemical modifications typically share the same polypeptide sequence. A substantially purified protein will typically comprise over about 85 to 90% of a protein sample, more usually about 95%, and preferably will be over about 99% pure. Protein purity or homogeneity may be indicated by a number of means well known in the art, such as polyacrylamide gel electrophoresis of a protein sample, followed by visualizing a single polypeptide band on a polyacrylamide gel upon staining. For certain purposes high resolution will be needed and HPLC or a similar means for purification utilized.

A polypeptide is substantially free of naturally-associated components when it is separated from the native contaminants which accompany it in its natural state. Thus, a polypeptide which is chemically synthesized or synthesized in a cellular system different from the cell from which it naturally originates will be substantially free from its naturally-associated components.

DETAILED DESCRIPTION

An isolated nucleic acid sequence, termed MIP-1α/RANTES receptor and the novel polypeptide which it encodes are described herein. Under stringent hybridization conditions, the intact isolated nucleic acids of this invention, particularly seq. I.D. No. 1, can be used as a probe to identify other mammalian MIP-1α/RANTES receptors. Under these conditions, the sequence does not cross-hybridize to non MIP-1α/RANTES receptor genes.

The nucleic acid compositions of this invention, whether RNA, cDNA, genomic DNA, or a hybrid of the various combinations, may be isolated from natural sources or may be synthesized in vitro. The preferred source for the MIP-1α/RANTES receptor gene is a human genomic library such as from livers, as available from Stratagene (La Jolla, Calif.).

The nucleic acids claimed may be present in transformed or transfected whole cells, in a transformed or transfected cell lysate, or in a partially purified or substantially pure form.

Nucleic acid probes are also included in the claimed invention. Such probes are useful for detecting the presence of MIP-1α/RANTES receptor in physiological samples, and as primers for gene amplification. The nucleic acid probes will usually be at least about 20 nucleotides in length, more typically they will be more than 500 nucleotides in length.

A method of isolating the MIP-1α/RANTES receptor is also described herein. Briefly, the nucleic acid sequences can be isolated by probing a DNA library which is comprised of either genomic DNA or cDNA. Libraries may be either from commercial sources or prepared from mammalian tissue by techniques known to those skilled in the art. The preferred cDNA libraries are human cDNA libraries derived from B cells or neutrophils which are available from commercial sources. These receptors are also found in non-human species, e.g. mammals. For non-human orthologous receptors, one probes the appropriate library.

The DNA libraries can be probed by plaque hybridization using nucleic acid probes of at least 20 base pairs which are complementary to unique sequences of the MIP-1α/RANTES receptor gene. A preferred probe is about 626 bases binding to base 259 to base 884 of Seq. I.D. No.1. The probes are labeled to facilitate isolation of the hybridized clones. Labeling can be by any of the techniques known to those skilled in the art. Typically the longer probes are labeled with $^{32}P$ using Klenow.

Alternatively, using the sequences provided herein, those of skill may use polymerase chain reaction technology (PCR) to amplify nucleic acid sequences of the MIP-1α/RANTES receptor gene directly from mRNA, from cDNA, from genomic libraries or cDNA libraries. Polymerase chain reaction (PCR) or other in vitro amplification methods may also be useful, for example, to clone nucleic acid sequences that code for proteins to be expressed, to make nucleic acids to use as probes for detecting the presence of MIP-1α/RANTES receptor in physiological samples, for nucleic acid sequencing, or for other purposes. Appropriate primers and probes for identifying MIP-1α/RANTES receptor from alternative mammalian tissues are generated from comparisons of the sequences provided herein. For a general overview of PCR see *PCR Protocols: A Guide to Methods and Applications*. (Innis, M, Gelfand, D., Sninsky, J. and White, T., eds.), Academic Press, San Diego (1990), incorporated herein by reference.

In summary, the MIP-1α/RANTES receptor gene can prepared by probing or amplifying selected regions of a mixed cDNA or genomic pool using the probes and primers generated from the sequences provided herein.

Through the use of recombinant DNA techniques one may express the MIP-1α/RANTES receptor gene in yeast, filamentous fungal cells, insect (especially employing baculoviral vectors), mammalian cells, and in bacterial systems. For this purpose, the natural or synthetic nucleic acids included in the invention will typically be operably linked to a promoter (which is either constitutive or inducible), and may be incorporated into an expression vector.

The isolated nucleic acid sequences can then be inserted into a cloning vector suitable for replication and integration in either prokaryotes or eukaryotes. The cloning vectors contain transcription and translation terminators, initiation sequences, and promoters useful for regulation of the expression of the MIP-1α/RANTES receptor gene. The vectors are comprised of expression cassettes containing at least one independent terminator sequence, sequences permitting replication of the plasmid in both eukaryotes and prokaryotes, i.e., shuttle vectors, and selection markers for both prokaryotic and eukaryotic systems.

Methods for the expression of cloned genes in bacteria are well known. To obtain high level expression of a cloned gene in a prokaryotic system, it is essential to construct expression vectors which contain, at a minimum, a strong promoter to direct mRNA transcription. The inclusion of selection markers in DNA vectors transformed in *E. coli* is also useful. Examples of such markers include genes specifying resistance to ampicillin, tetracycline, or chloramphenicol. See Sambrook for details concerning selection markers and promoters for use in *E. coli.*

It is expected that those of skill in the art are knowledgeable in the expression systems chosen for expression of the MIP-1α/RANTES receptor gene and no attempt to describe in detail the various methods known for the expression of proteins in eukaryotes will be made.

Suitable eukaryote hosts may include plant cells, insect cells, mammalian cells, yeast, filamentous fungi, or preferably, bacteria (e.g., *E. coli* or *B. subtilis*).

The protein encoded by the MIP-1α/RANTES receptor gene which is produced by recombinant DNA technology may be purified by standard techniques well known to those of skill in the art. Standard techniques include selective precipitation with such substances as ammonium sulfate, column chromatography, immunopurification methods, and others. See, for instance, R. Scopes, *Protein Purification: Principles and Practice*, Springer-Verlag: New York (1982), incorporated herein by reference.

Alternatively and preferably, fusion proteins produced by the above method may be purified by a combination of sonication and affinity chromatography. Subsequent digestion of the fusion protein with an appropriate proteolytic enzyme releases the desired polypeptide.

The MIP-1α/RANTES receptor gene appears in the human population in various forms. By following the methods disclosed herein, one can evaluate the polymorphisms. The invention describes a single sequence encoding MIP-1α/RANTES receptor. Polymorphic forms are also intended to be included. These forms are obtained by using the given sequence as probe under stringent conditions to assay a genomic library. Polymorphic variants of the MIP-1α/RANTES receptor genes are obtained by comparing the sequences of other genes hybridizing to the original sequence.

The present invention also provides methods for detecting the presence or absence of MIP-1α/RANTES receptor in a physiological specimen.

One method involves a Southern transfer and is well known to those of skill in the art. Briefly, the digested genomic DNA is run on agarose slab gels in buffer and transferred to membranes. Hybridization is carried out using the probes discussed above. Visualization of the hybridized portions allows the qualitative determination of the presence or absence of MIP-1α/RANTES receptor.

Similarly, a Northern transfer may be used for the detection of MIP-1α/RANTES receptor in samples of RNA. This procedure is also well known in the art. See, Maniatis, et al., *Molecular Cloning: A laboratory manual*, Cold Spring Harbor Laboratory, Cold Spring Harbor, N.Y. (1982). In brief, the mRNA is isolated from a given cell sample using an acid guanidinium-phenol-chloroform extraction method. The mRNA is then electrophoresed to separate the mRNA species and the mRNA is transferred from the gel to a nitrocellulose membrane. As with the Southern blots, labeled probes are used to identify the presence or absence of the MIP-1α/RANTES receptor transcript.

An alternative means for determining the level of expression of the MIP-1α/RANTES receptor gene is in situ hybridization. In an in situ hybridization cells are fixed to a solid support, typically a glass slide. If DNA is to be probed the cells are denatured with heat or alkali. The cells are then contacted with a hybridization solution at a moderate temperature to permit annealing of MIP-1α/RANTES receptor specific probes that are labelled. The probes are preferably labelled with radioisotopes or fluorescent reporters. In situ hybridization assays are well known and are generally described in Angerer, et al., *Methods Enzymol.*, 152:649–660 (1987).

In addition to the detection of MIP-1α/RANTES receptor using nucleic acid hybridization technology, one can use immunoassays to detect the MIP-1α/RANTES receptor gene product. Immunoassays can be used to qualitatively and quantitatively analyze the MIP-1α/RANTES receptor gene product. A general overview of the applicable technology can be found in Harlow and Lane, *Antibodies: A Laboratory Manual*, Cold Spring Harbor Pubs., N.Y. (1988). In brief, the gene product or a fragment thereof is expressed in transfected cells, preferably bacterial cells, and purified as generally described above and in the examples. The product is then injected into a mammal capable of producing antibodies. Either monoclonal or polyclonal antibodies specific for the gene product can be used in various immunoassays. Such assays include ELISA, competitive immunoassays, radioimmunoassays, western blots, indirect immunofluorescent assays and the like.

Finally, the MIP-1α/RANTES receptor can be functionally expressed on the surface of mammalian cells and these cells used to directly assay for MIP-1α or RANTES in biological samples. The quantitation of MIP-1α or RANTES is useful for monitoring the levels of these cytokines in a patient. Such measurements are useful in following the anti-inflammatory effects of drugs and prospective usefulness of new anti-inflammatory agents.

Functional expression of eukaryote proteins is well known. The methods are as followed in typical transection protocols such as described in Sambrook. In brief, such assays are produced by transforming cells such as COS cells, 293 cells, 3T3 fibroblast cells, and yeast cells. Alternatively oocytes, typically from frogs can be microinjected with synthetic RNA (copy RNA). The cells are transformed with a suitable expression vector or a suitable amount of synthetic or copy RNA to effect expression of the MIP-1α/RANTES receptor on the cell's plasma membrane. The cells are then exposed to labelled MIP-1α or RANTES and the amount of binding assayed either by fluorescent microscopy or autoradiography. Alternatively, binding of MIP-1α or RANTES to the cells will result in a calcium efflux and this can be measured as described below.

Fluid samples from patients suffering from inflammatory diseases are taken using standard methods. These fluids include plasma, synovial fluid, abscess fluid, bronchopulmonary lavage fluid and the like. For example, synovial fluid from an arthritic joint could be assayed for the presence of elevated amounts of MIP-1α or RANTES. As the disease progresses or is abated by drug therapies, the relative amount of MIP-1α or RANTES will change and the concentration changes would be reflected in the binding assays described above.

The following examples are provided by way of illustration only and not by way of limitation. Those of skill will readily recognize a variety of noncritical parameters which could be changed or modified to yield essentially similar results.

EXAMPLES

Example 1: Screening a Genomic Library for the MIP-1α/RANTES Receptor i. PCR Amplification of a MIP-1α/RANTES Probe The DNA sequence encoding the MIP-1α/RANTES receptor may be isolated from a human genomic or cDNA library using a DNA probe specific to a portion of that sequence. A preferred probe encoding a 626 base pair portion of the coding block of the MIP-1α/RANTES receptor gene may be amplified by polymerase chain reaction (PCR) from human genomic DNA using a pair of primers corresponding to sequences from base 259 to 275 and from base 868 to 884 of sequence I.D. No. 1. The PCR reaction solution consists of 67 to 71 μl of water, 10 μl of 10× buffer, 8 μl dNTPs (10 mM stock concentration each for dATP, dCTP, dGTP, dTTP in a master mix, final concentration=2 mM each, Perkin-Elmer Cetus, Emeryville, Calif.), 5 μl each of 20 μM sense and antisense primer (final concentration each=1 μM), 1–5 μl DNA, and 1 μl Taq DNA polymerase (Boehringer-Mannheim, Indianappolis) to provide a total volume of 100 μl. The PCR conditions are 95° C. for 5 min; 30 cycles of 94° C. for 20 sec then 55° for 20 sec, and 72° C. for 1 min. Cycling occurs in a GeneAmp Thermocycler from Perkin Elmer/Cetus.

ii. Screening a Genomic Library

Using the above described probe, a human fetal liver genomic library (Stratagene, La Jolla, Calif.) is screened by plaque hybridization with a $^{32}P$-labeled probe specific to a segment of the DNA encoding the MIP-1α/RANTES receptor. Hybridization occurs in a buffer containing 50% formamide, 5× SSPE, 0.5% SDS, 50 μg/ml denatured salmon sperm DNA and $10^6$ cpm/ml of labeled probe at 37° C. for 20 hours. The filters are washed in 5× SSPE at 45° C. for 1 hour. Positive clones are then purified and their sequences verified in comparison with Seq. I.D. No. 1.

Example 2: Synthesis of MIP-1α/RANTES Receptor Protein cRNA

In our laboratory, the given sequence was identified and cloned without pre-knowledge of the actual sequence. From this sequence a copy RNA was produced and its ability to generate a suitably sized protein checked by in vitro synthesis. The cRNA was synthesized by in vitro transcription with T3 RNA polymerase of a Bluescript construct that had been cleaved with Xho I.

Example 3: Functional Expression and Calcium Efflux Assay

The materials and methods used for the calcium efflux assay were as described in Murphy, et al., *J. Immunol.* 145:2227–2234 (1990). Adult female laboratory bred *Xenopus laevis* (Nasco, Fort Atkinson, Wis.) were maintained at 19° C. to 22° C. in a light-dark cycle of 12 h per phase. The frogs were anesthetized and ovarian lobes were resected and defolliculated in OR2 solution (82.5 mM NaCl, 1 mM $MgCl_2$, 2.4 mM KCl, 5 mM HEPES, pH 7.5) containing 2 mg/ml collagenase for 2 h on a rotary shaker. Stage V–VI oocytes were transferred to ND96 solution (96 mM NaCl, 2 mM KCl, 1.8 mM $CaCl_2$, 1 mM MgCl2, 2.4 mM sodium pyruvate, penicillin 100 U/ml, streptomycin 100 μg/ml, 5 mM HEPES, pH 7.4 to 7.5).

After 1–2 days, oocytes were microinjected with RNA samples in a total volume of 50 nl per oocyte and were then incubated in ND96 solution at 20° C. to 23° C. for 3 to 5 days. Oocytes were then incubated in 500 μl of OR2 medium containing $^{45}Ca^{2+}$ [50 μCi/ml (ICN Biomedicals, Costa Mesa, Calif.)] for 3 hours at 20° C. After ten washes with ND96 medium, individual oocytes were stimulated with ligand in wells of a 96-well tissue culture plate containing 100 μl of ND96 medium. Three 100 μl samples of the incubation medium were collected and analyzed by liquid scintillation counting: a) the final 100 μl wash (20 min) before application of ligand; b) fluid containing the stimulus, removed after a 20 min incubation with the oocyte; and c) the oocyte solubilized in SDS (1%) in medium 20 min after stimulation. Data are presented as the mean±standard error of the mean (SEM) of the percent of loaded $^{45}Ca^{2+}$ that was released by individual oocytes in response to the stimulus, or $[(b-a)\div(b+c)]\times 100$.

Ligands were all human recombinant material obtained from the following sources: MIP-1α (R and D Systems, Minneapolis, Minn.); IL-8, RANTES, and MCAF (Genzyme, Cambridge, Mass.); NAP-2 (Bachem Bioscience, Philadelphia, Pa.); GRO-α (a gift from M. P. Beckmann, S. Lyman and D. Cerretti). MIP-1α and MIP-1β used in a ligand screen was a gift of U. Siebenlist (NIAID, Bethesda, Md.) and were used as a diluted supernatant of Sf9 insect cells expressing immunoreactive recombinant human MIP-1α (from clone pAT464) or MIP-1β (from clone pAT744) that was prepared as described in Zipfel et al. *J. Immunol.* 142:1582–1590 (1989) and Zipfel et al. *Lymph. Cyto. Res.* 11:141–148 (1992). All proteins were diluted from aqueous stock solutions or culture supernatants into ND96 oocyte media (96 mM NaCl, 1 mM KCl, 1 mM $MgCl_2$. ⅛ mM $CaCl_2$, pH 7.45) containing 0.1% bovine serum albumin.

Figure 1B:
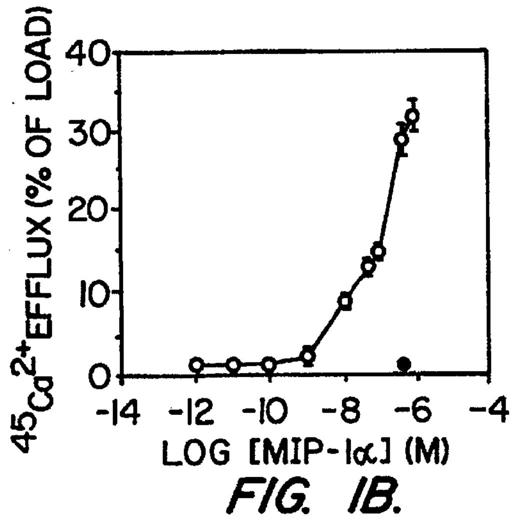
Figure 1C:
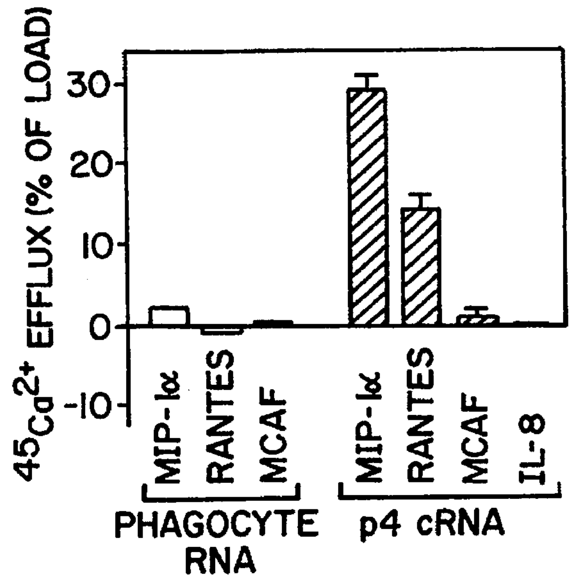

Oocytes injected with cRNA acquired responsiveness to MIP-1α and RANTES, but not to MIP-1β, MCP-1, IL-8, GROα, or NAP-2 (FIG. 1).

More specifically the data presented in FIG. 1 demonstrates that a signal transduction is associated with the MIP-1α/RANTES receptor. (A) The MIP-1α/RANTES receptor cDNA encodes a receptor selective for an intercrine β ligand. Five days after injection with 10 ng of either MIP-1α/RANTES receptor cRNA (closed bars) or IL-8 receptor B cRNA (open bars), oocytes were stimulated with recombinant human IL-8, GRO-$\alpha$ or NAP-2 at 500 nM, or a 1:5 dilution of an Sf9 supernatant containing recombinant human MIP-1$\alpha$ or MIP-1$\beta$. Prostaglandin E2, histamine, C5a, f-met-leu-phe, ATP, UTP and platelet activating factor were also tested and were inactive. Neither MIP$\alpha$ nor MIP-1$\beta$ activated the IL-8 receptor B. (B) Concentration dependence for MIP-1$\alpha$ calcium mobilizing activity. Oocytes injected with 50 ng HL-60 RNA (closed circle) or 10 ng of MIP-1$\alpha$/RANTES receptor cRNA (open circle) were stimulated with the indicated concentration of recombinant human MIP-1$\alpha$. (C) The MIP-1$\alpha$ receptor is also a receptor for RANTES. Oocytes were injected with either HL-60 RNA (open bars) or MIP-1$\alpha$/RANTES receptor cRNA (closed bars) and stimulated with the indicated ligand at 250 nM. In panels A–C, the data derive from 5–8 replicate determinations per point. Basal amounts of calcium efflux and calcium uptake were similar for all experimental conditions.

From our studies, the $EC_{50}$ for RANTES was approximately 50 nM. The oocyte response to MIP-1$\alpha$ had two phases, one that appeared to saturate at 100 NM MIP-1$\alpha$, and a second that did not reach a plateau at 5000 nM MIP-1$\alpha$.

Example 4: Radioligand Binding Assay

Carrier free recombinant human MIP-1$\alpha$ 10 $\mu$g (Genzyme, Cambridge, Mass.) was labeled using 5 mCi $Na^{125}I$ (Amersham, Arlington Heights, Ill.) in 100 $\mu$l 0.2M sodium phosphate, pH 7.2 and 50 $\mu$l reconstituted Enzymobeads (BioRad, Richmond, AC). The reaction was started using 25 $\mu$l 1% $\beta$-D-glucose and allowed to continue for 20 minutes. Labeled sample was separated from the free iodine using a NAP-5 column (Pharmacia LKB, Piscataway, N.J.) which had been previously rinsed with 1% bovine serum albumin in 0.2M sodium phosphate, pH 7.2. Labeled material was collected from the column and analyzed on a 14% acrylamide gel. Single oocytes were incubated with $^{125}I$-MIP-1$\alpha$ for 30 min on ice in 10 $\mu$l of binding buffer (Hanks' balanced salt solution with 25 mM HEPES, 1% bovine serum albumin, pH 7.4). Unbound ligand was removed by centrifugation of the oocyte through 300 $\mu$l of F50 silicone fluid (General Electric, Waterford, N.Y.). The tubes were quickly frozen and gamma emissions from the amputated tips were counted.

Figure 2A:
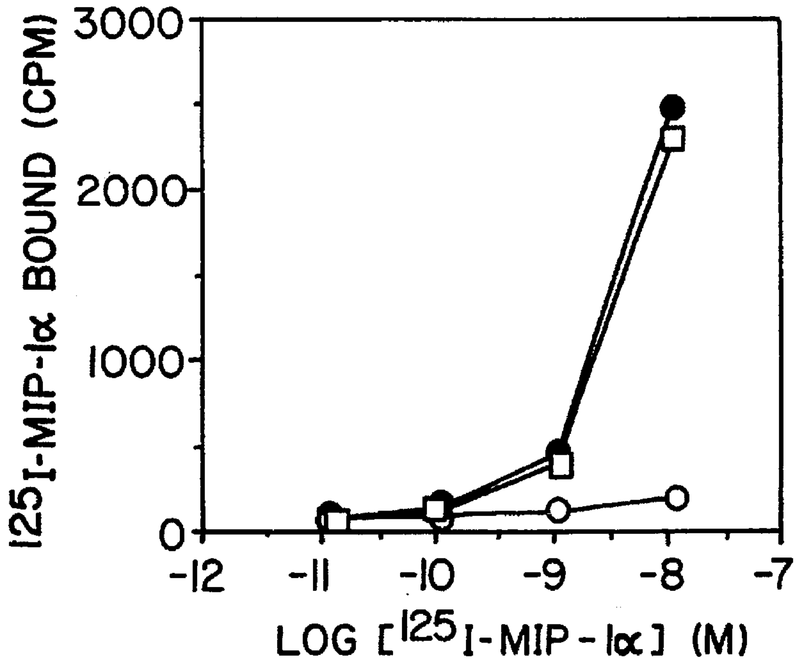
FIGS. 2A–B. Binding of $^{125}$I-labeled MIP-1α to oocytes injected with p4 cRNA. (A) Total (closed circles) and non-specific binding (open circles) was determined. (B) Competitive assays involving a MIP-aα radioligand. More specifically, oocyte injected with MIP-1α/RANTES cRNA were incubated with 100,000 cpm $^{125}$I-labeled MIP-1α in the presence or absence of unlabeled MIP-1α.
Figure 2B:
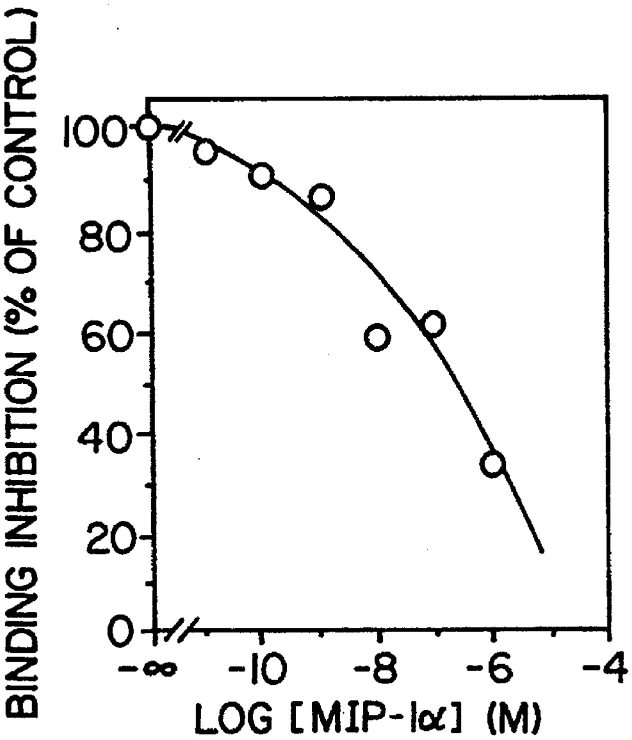

The results of the binding assays are presented in FIG. 2. Binding of $^{125}I$-labeled MIP-1$\alpha$ to oocytes injected with MIP-1$\alpha$/RANTES receptor cRNA. (A) Total (closed circles) and non-specific binding (open circles) was determined by incubating oocytes injected with MIP-1$\alpha$/RANTES receptor cRNA with the indicated concentration of $^{125}I$-labeled MIP-1$\alpha$ in the absence or presence of a 100 fold molar excess of unlabeled MIP-1$\alpha$, respectively. Non-specific binding was subtracted from total binding to determine specific binding (open squares). Specific binding of $^{125}I$-labeled MIP-1$\alpha$ to oocytes expressing IL-8 receptor B was undetectable. (B) Oocytes injected with MIP-1$\alpha$/RANTES receptor cRNA were incubated with 100 nM $^{125}I$-labeled MIP-1$\alpha$ in the presence or absence of the indicated concentration of unlabeled MIP-1$\alpha$. One hundred percent represents a mean of 6401 cpm. Data are derived from triplicate determinations per point.

The threshold for detection of specific binding of $^{125}I$-MIP-1$\alpha$ to oocytes injected with the MIP-1$\alpha$/RANTES receptor cRNA was the same as that required for stimulation of calcium efflux. $^{125}I$-MIP-1$\alpha$ did not bind specifically to oocytes expressing human IL-8R B.

What is claimed is:

1. A substantially purified nucleic acid encoding a receptor for macrophage inflammatory protein-1α (MIP-1α) and regulated upon activation normal T expressed and secreted (RANTES) protein said nucleic acid capable of selectively hybridizing to a second nucleic acid consisting of the complement of the nucleotide sequence of Sequence I.D. No. 1 in the presence of a human genomic library under stringent conditions of 68° C. and 0.1× SSC or SSPE.

2. A substantially purified nucleic acid of claim 1 encoding the polypeptide of Sequence I.D. No. 2.

3. A subsequence of the nucleic acid of claim 1 having at least 12 contiguous nucleotides, said nucleic acid capable of selectively hybridizing to a second nucleic acid consisting of the complement of the nucleotide sequence of Sequence I.D. No. 1 in the presence of a human genomic library under stringent conditions of 68° C. and 0.1× SSC or SSPE.

4. A substantially purified nucleic acid of claim 1, wherein a promoter is operably linked to the nucleic acid.

5. A nucleic acid of claim 4, wherein the promoter and the nucleic acid are contained in an expression vector.

6. A cell transformed or transfected with a nucleic acid of claim 5.

7. A cell transformed or transfected with a nucleic acid of claim 1.

8. A cell of claim 7, wherein the cell is mammalian.

9. A cell of claim 8 wherein the cell is expressing the MIP-1α/RANTES receptor gene product and transporting the product in a biologically active form to its plasma membrane.

10. A substantially purified polypeptide having an amino acid sequence substantially identical to a polypeptide of Sequence I.D. No. 2.

11. A substantially purified nucleic acid wherein said nucleic acid consists of the nucleotide sequence of Sequence I.D. No. 1.

12. A substantially purified polypeptide consisting of the amino acid sequence of Sequence I.D. No. 2.

* * * * *